United States Patent [19]
Marshak et al.

[11] Patent Number: 5,908,782
[45] Date of Patent: *Jun. 1, 1999

[54] CHEMICALLY DEFINED MEDIUM FOR HUMAN MESENCHYMAL STEM CELLS

[75] Inventors: Daniel R. Marshak, Cold Spring Harbor, N.Y.; James J. Holecek, Solon, Ohio

[73] Assignee: Osiris Therapeutics, Inc., Baltimore, Md.

[*] Notice: This patent issued on a continued prosecution application filed under 37 CFR 1.53(d), and is subject to the twenty year patent term provisions of 35 U.S.C. 154(a)(2).

[21] Appl. No.: 08/464,599

[22] Filed: Jun. 5, 1995

[51] Int. Cl.[6] ............... C12N 5/00; C12N 5/08; A61K 35/12

[52] U.S. Cl. ............ 435/366; 424/93.7; 435/371; 435/383; 435/384; 435/388; 435/389; 435/404; 435/405; 435/407; 435/372

[58] Field of Search ............... 424/93.7, 93.1; 435/69.4, 70.3, 240.1, 240.2, 240.3, 240.21, 366, 371–372, 383, 388, 384, 389, 404, 405, 407; 530/363

[56] References Cited

U.S. PATENT DOCUMENTS

| | | | |
|---|---|---|---|
| 4,444,778 | 4/1984 | Coughlin | 514/280 |
| 5,045,467 | 9/1991 | Bertheussen | 435/404 |
| 5,197,985 | 3/1993 | Caplan et al. | 623/16 |
| 5,486,359 | 1/1996 | Caplan et al. | 424/93.7 |

OTHER PUBLICATIONS

Seuwen et al., Serotonin stimulates DNA synthesis in fibroblasts acting through 5–HT receptors coupled to G–protein, Nature 335, pp. 254–256. Sep. 1988.

Brower et al. Growth of Cell Lines and Clinical Specimens of Human Non–Small Cell Lung Cancer in a Serum–Free Defined Medium, Cancer Res. 46:798–806. 1986.

Jessop et al. The differentiation of a potential mesenchymal stem cell population within ovine bone marrow. Biochem Soc Transactions 22:248S. 1994.

Maurer. Towards Chemically–defined, serum–free media for mammalian cell culture. In: Animal cell culture a practical approach (Freshney, ed.) pp. 13–19. (1986).

*Primary Examiner*—Leon B. Lankford, Jr.
*Assistant Examiner*—Christopher Tate
*Attorney, Agent, or Firm*—Elliot M. Olstein; Raina Semionow

[57] ABSTRACT

A composition and method for maintaining the viability of human mesenchymal precursor cells in a serum-free environment which composition includes (1) a minimum essential medium; (2) serum albumin; (3) an iron source; (4) insulin or an insulin-like growth factor; and (5) at least one amino acid selected from the group consisting of glutamine, arginine and and cysteine, and is free of serum. Also, a composition and method for culture expanding human mesenchymal precursor cells in a serum-free environment. This composition further includes a mitogen, paricularly a serotonergic agonist. The cells are preferably isolated human mesenchymal stem cells.

12 Claims, 4 Drawing Sheets

CHEMICALLY DEFINED MEDIUM FOR HUMAN MESENCHYMAL STEM CELLS

This invention relates to the field of cell and tissue culture media, particularly to such media which can support viability and/or growth of cells in the absence of serum.

Bone marrow is a complex tissue composed of hematopoietic, endothelial and stromal elements. Marrow stroma consists of a network of cells and matrix which provide the physical scaffold and a suitable chemical environment for hematopoiesis. Included in the stromal cell population are fibroblasts, reticulocytes, adipocytes and osteogenic cells. It has been postulated that, within the marrow stromal cell population, stem cells exist which have fibroblastic, adipogenic, reticular, osteogenic or chondrogenic potential. These cells are referred to as mesenchymal stem cells (MSCs). The development of bone and cartilage in diffusion chamber assays following the introduction of whole marrow, suspensions of marrow cells or cultured marrow-derived mesenchymal cells supports the notion that MSCs are osteochondral progenitor cells that can be isolated from, inter alia, bone marrow. Whole marrow and cultured marrow-derived fibroblastic cells have also given rise to bone and cartilage when combined with porous tricalcium phosphate-hydroxyapatite ceramic cubes which were then implanted subcutaneously into syngeneic or immuno-compromised hosts.

Bone formation has been observed when cultured marrow-derived MSCs from human, rat, murine, canine, rabbit and avian donors were used in the ceramic cube assay. Cells from all of these sources were maintained in vitro in serum-supplemented medium. Serum plays a critical role in the growth of cells in vitro by providing components such as amino acids, lipids, growth factors, vitamins, hormones and attachment factors, by acting as a pH buffer and by providing protease inhibitors (Barnes and Sato, *Anal. Biochem.*, 102:270, 1980; Iscove, In *Cell Culture Methods for Molecules and Cell Biology* (ed. D. W. Barnes et al.), pp. 169–185, 1984; and Barnes, *BioTechniques*, 5:534–541, 1987). Nevertheless, the high degree of variability of different lots of serum, the relatively poor degree of characterization of serum components and the necessity of laboriously testing serum prior to its purchase makes the replacement of serum by a chemically defined medium highly desirable.

The growth and expansion of these MSC is accomplished using a nutrient medium fortified with fetal bovine serum. Although serum supplementation is useful in that it provides the cells-with nutrients, attachment factors, and growth factors necessary for their in vitro survival (Barnes supra, 1980 & 1987; Iscove, supra, 1984), the use of serum is problematic in that there is high cost, lot to lot variation, and a costly screen process is required. In addition to the time and cost problems, the use of serum also adds complexity to any studies which investigate the effect peptide growth factors and small molecules have on the differentiation and growth of cells in vitro. At present there is a chemically defined medium for the growth and expansion of rat marrow derived mesenchymal stem cells (Lennon et al. 1995, submitted) and several for human marrow hematopoietic stem cells (Iscove supra, 1984; Drouet et al., *Br. J. Hematol.*, 73:143–147, 1989; and Sandstrom et al., *Biotechnology and Bioengineering*, 43:706–733, 1994) but not one that would support the growth of human MSCs.

The invention is based on the discovery by the inventors of a composition of chemically defined components which support viability and/or growth of mesenchymal progenitor cells in the absence of serum.

Thus, in one aspect the invention provides a composition for maintaining the viability of human mesenchymal precursor cells in a serum-free environment which composition comprises (1) a minimum essential medium; (2) serum albumin; (3) an iron source; (4) insulin or an insulin-like growth factor; and (5) glutamine, and which is free of serum. This aspect also contemplates such a composition in aqueous liquid form in combination with at least one human mesenchymal progenitor cell, particularly an isolated human mesenchymal stem cell.

The invention also provides a method for maintaining the viability of human mesenchymal precursor cells in a serum-free environment which method comprises maintaining viabile human mesenchymal precursor cells in a medium which is free of serum and which comprises (1) a minimum essential medium; (2) serum albumin; (3) an iron source; (4) insulin or an insulin-like growth factor; and (5) glutamine, and which is free of serum.

The invention also provides a composition for culture expanding human mesenchymal precursor cells in a serum-free environment which composition comprises (1) a minimum essential medium; (2) serum albumin; (3) an iron source; (4) insulin or an insulin-like growth factor; (5) glutamine; and (6) a mitogen, and which is free of serum. This aspect also contemplates such a composition in aqueous liquid form in combination with at least one human mesenchymal progenitor cell, particularly an isolated human mesenchymal stem cell.

The invention also provides a method for culture expanding human mesenchymal precursor cells in a serum-free environment which method comprises culturing viabile human mesenchymal precursor cells in a medium which is free of serum and which comprises (1) a minimum essential medium; (2) serum albumin; (3) an iron source; (4) insulin or an insulin-like growth factor; (5) glutamine; and (6) a mitogen, and which is free of serum.

The invention will now be further described by reference to a brief description of each of the Figures, but in no way are a limitation of the scope of the invention.

FIGS. 4A and 4B graphically illustrate the level of osteogenic differentiation, as measured by alkaline phosphatase of hMSCs grown in Chemically Defined Medium or in Complete Medium with and without Osteogenic Supplements (OS), as follows:

The invention will now be described in more detail with respect to numerous embodiments and examples in support thereof.

As used herein the term "minimum essential medium" refers to any serum-free animal cell culture preparation or medium of known composition which will support the viability of human mesenchymal stem cells in vitro. Examples are any of the Eagle's based media, i.e., Dulbecco's Modified Eagle's Medium (DMEM); Iscove's Modified Eagle's Medium, alpha Modified Eagle's Medium, and also McCoy's 5A and $BGJ_b$ (Fitton-Jackson Modification).

As used herein the term "albumin" refers to serum albumin of any mammalian species, but not to other forms of albumin, such as ovalbumin, lactalbumin, or grain or soybean albumins.

As used herein the term "iron source" refers to any species that will release the reduced, ferric, form of iron to the medium, including but not limited to transferrin, $FeSO_4$ or ferritin.

As used herein the term "insulin" refers to any of the various insulins that are known. Insulins are divided into three categories according to promptness, duration and intensity of action following subcutaneous administration, i.e., as mentioned above, rapid, intermediate or long-acting. Crystalline regular insulin is prepared by precipitation in the presence of zinc chloride and modified forms have been developed to alter the pattern of activity. Protamine zinc insulin (PZI) is the result of the reaction of insulin and zinc with the basic protein, protamine, to form a protein complex which dissolves and is absorbed more slowly than crystalline regular insulin but is highly reliable for absorption at a steady rate. Isophane is a modified crystalline protamine zinc insulin whose effects are comparable to a mixture of predominantly regular insulin with a lesser portion of protamine zinc insulin. The extended and prompt insulin-zinc suspensions are also contemplated for use in the invention. The insulin can be, for example, of human bovine, ovine or other animal origin or can be a recombinant product.

Human insulin is now widely available as a result of its production by recombinant DNA techniques; in theory it should be slightly less immunogenic than purified porcine insulin, which in turn should be less immunogenic than bovine insulin. Bovine insulin differs from human insulin by three amino acid residues, whereas porcine differs from human insulin by only one amino acid at the carboxyl-terminus of the B chain. However, when highly purified, all three insulins have a relatively low, but measurable, capacity to stimulate the immune response.

Short- or rapid-acting insulins are simply solutions of regular, crystalline zinc insulin (insulin injection) dissolved in a buffer at neutral pH. These have the most rapid onset of action but the shortest duration, i.e., glucose levels reach a low point within 20–30 minutes and return to baseline in about 2–3 hours.

Intermediate-acting insulins are formulated so that they dissolve more gradually when administered subcutaneously; their durations of action are thus longer. The two preparations most frequently used are neutral protamine Hagedorn (NPH) insulin (isophane insulin suspension) and Lente insulin (insulin zinc suspension). NPH insulin is a suspension of insulin in a complex with zinc and protamine in a phosphate buffer. Lente insulin is a mixture of crystallized (Ultralente) and amorphous (Semilente) insulins in an acetate buffer, which minimizes the solubility of insulin. The preparations have similar pharmacokinetic profiles.

Ultralente insulin (extended insulin zinc suspension) and protamine zinc insulin suspension are long-acting insulins; they have a very slow onset and a prolonged ("flat") peak of action. These insulins are advocated to provide a low basal concentration of insulin throughout the day.

As used herein the term insulin is also contemplated to encompass insulin analogs. Recent development of insulin that have altered rates of absorption have raised interest. Insulin with aspartate and glutamate substituted at positions B9 and B27, respectively, crystallizes poorly and has been termed "monomeric insulin". This insulin is absorbed more rapidly from subcutaneous depots and thus may be useful in meeting postprandial demands. By contrast, other insulin analogs tend to crystallize at the site of injection and are absorbed more slowly. Insulins with enhanced potency have been produced by substitution of aspartate for histidine at position B10 and by modification of the carboxyl-terminal residues of the B chain.

As used herein the terms "somatomedin(s)" or "insulin-like growth factor(s)" refer to peptide hormones structurally related to human proinsulin. Insulin-like growth factor-I or SM-C is a basic, 7649-molecular-weight, 70-amino acid, growth hormone (GH)-dependent, single-chain peptide. Insulin-like growth factor-II is a 67-amino acid. 7471-molecular-weight neutral peptide structurally similar to IGF-I, but much less GH dependent. Both peptides demonstrate stimulation of sulfate incorporation into cartilage, insulin-like activity in muscle and adipose tissue, and mitogenic activity, particularly in fibroblasts. Circulatory SM-C is primarily synthesized by the liver. Receptors for IGF peptides have been detected in most cells. Two types of receptors have been described. Type I receptor shows a high affinity for IGF-I, a somewhat lower affinity for IGF-II, and a low affinity for insulin. Type II receptor has a high affinity for IGF-II, a low to moderate affinity for IGF-I, and no affinity for insulin. Binding of the growth factor to its receptor causes autophosphorylation of receptor tyrosine residues. IGFs regulate the synthetic activity of cells. In cartilage, IGFs stimulate sulfate and leucine uptake into glycosaminoglycans and proline conversion to hydroxyproline. In adipocytes, IGFs show insulin-like activity including stimulation of glycolysis, inhibition of lipolysis, and inhibition of glycogenolysis.

As used herein the term "growth factor" refers to proteins that cause resting cells to undergo cell division and, in some cases, differentiation. Some growth factors are cell type-specific, stimulating division of only those cells with appropriate receptors; other growth factors are more general in their effects. Among the well-studied growth factors are epidermal growth factor (EGF), nerve growth factor (NGF), fibroblast growth factor (FGF), platelet-derived growth factor (PDGF), erythropoietin, and a family of proteins called lymphokines, which includes interleukins (IL-1, IL-2, etc.) and interferon γ. There are also extracellular factors that antagonize the effects of growth factors, slowing or preventing cell division; transforming growth factor β (TGFβ) and tumor necrosis factor (TNF) are such factors.

Platelets are the main source of mitogenic activity found in whole blood serum and missing in plasma. The growth factor with this mitogenic activity is platelet-derived growth factor (PDGF). PDGF has a molecular weight of 28,000 to 35,000. It is made up of two chains, which share 60% homology. The A chain has a molecular weight of 17,000. The B chain is sufficient for the mitogenic effect of PDGF.

Platelet-derived growth factor is a mitogen for cells bearing its receptor and acts synergistically with other growth factors as a competence factor. Platelet-derived growth factor nonreciprocally inhibits EGF binding to the EGF receptor, and stimulates the production and release of somatomedin-C (SM-C)-like factor by cultured human fibroblasts and porcine aorta smooth-muscle cells. Therefore, PDGF modulates growth factor synthesis, secretion, and effects at a tissue level.

A particularly preferred growth factor for use in the hCDM is platelet-derived growth factor, particularly the ββ homodimer of human recombinant platelet-derived growth factor(hrPDGFββ).

As used herein the term "antioxidant" refers to any substance that slows down the oxidation of hydrocarbons, oils, fats or the like and thus helps to delay or prevent deterioration. Examples include ascorbic acid and its analogues, particularly ascorbic acid-2-phosphate. Other categories of antioxidants include monothiogycerol, pyruvic acid, citric acid, and retinol acetate.

As used herein the term "antibiotic/antimycotic" refers to preparations of antibacterial and antifungal agents that are typically used in human and animal tissue culture.

As used herein the term "essential amino acids" refers to glutamine or commercially available stabilized analogs, such as GlutaMax-I supplement (GIBCO) which can be used in lieu of glutamine.

As used herein the term "lipid" refers to biological lipids. Biological lipids are a chemically diverse group of compounds which are insoluble or only very slightly soluble in water. Their biological functions are equally diverse. Fats and oils are the principal stored forms of energy in many organisms, and phospho-lipids and sterols make up about half the mass of biological membranes. Other lipids, although present in relatively small quantities, play crucial roles as enzyme cofactors, electron carriers, light-absorbing pigments, hydrophobic anchors, emulsifying agents, hormones, and intracellular messengers.

As used herein the term "fatty acid" refers to long chain carboxylic acids which generally contain 4–36 carbon atoms and preferably contain at least 12 carbon atoms, most preferably 12 to 22. In some cases this carbon chain is fully saturated and unbranched, while others contain one or more double bonds. They can have saturated, unsaturated, branched or straight chain hydrocarbon chains. A few contain 3-carbon rings or hydroxyl groups. The compounds are generally not surface active. They are poorly soluble in water and the longer the acid chain, the fewer the double bonds, the lower the solubility in water. The carboxylic acid group is polar and ionized at neutral pH. This accounts for the slight solubility of short-chain acids in water.

Examples of such acids are those ranging from $C_{16}$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, palmitoleic, acid gadoleic acid and erucic acid. Also useful are unsaturated (polyolefinic) straight chain monocarboxylic acids. Examples of these are linoleic acid, ricinoleic acid, linolenic acid, arachidonic acid and behenolic acid. Useful branched acids include, for example, diacetyl tartaric acid.

The physical properties of the fatty acids, and of compounds that contain them, are largely determined by the length and degree of unsaturation of the hydrocarbon chain. The nonpolar hydrocarbon chain accounts for the poor solubility of fatty acids in water. The longer the fatty acyl chain and the fewer the double bonds, the lower the solubility in water. The carboxylic acid group is polar (and ionized at neutral pH), and accounts for the slight solubility of short-chain fatty acids in water.

In mammals, free fatty acids (having a free carboxylate group) circulate in the blood bound to a protein carrier, serum albumin. However, fatty acids are present mostly as carboxylic acid derivatives such as esters or amides. Lacking the charged carboxylate group, these fatty acid derivatives are generally even less soluble in water than are the free carboxylic acids.

The simplest lipids constructed from fatty acids are the triacylglycerols, also referred to as triglycerides, fats, or neutral fats. Triacylglycerols are composed of three fatty acids each in ester linkage with a single glycerol (FIG. 9-2). Those containing the same kind of fatty acid in all three positions are called simply triacylglycerols, and are named after the fatty acid they contain. In most eukaryotic cells, triacylglycerols form a separate phase of microscopic, oily droplets in the aqueous cytosol, serving as depots of metabolic fuel.

As used herein the term "lipoprotein" refers to a conjugated protein formed from a lipid prosthetic group bound to an apolipoprotein. Apolipoproteins are lipid-binding proteins in the blood, responsible for the transport of triacylglycerols, phospholipids, cholesterol, and cholesteryl esters between organs. Apolipoproteins ("apo" designates the protein in its lipid-free form) combine with various lipids to form several classes of lipoprotein particles, spherical aggregates with hydrophobic lipids at the core and hydrophilic protein side chains and lipid head groups at the surface. Various combinations of lipid and protein produce particles of different densities, ranging from chylomicrons and very low-density lipoproteins (VLDL) to very high-density lipoproteins (VHDL), which may be separated by ultracentrifugation.

As used herein the term "non-essential amino acids" refers to the remainder of the known naturally-occuring amino acids that participate in physiological processes and are used in protein synthesis.

As used herein the term "mitogen" refers to a substance that stimulates mitosis and/or lymphocyte transformation.

Phospholipids such as lecithin, myoinositol, phosphatidylethanolamine, sphingomyelin and phosphatidyl choline can be added to supplement their availability for cell membrane synthesis. A suitable source is the the product "Ex-Cyte" (Miles, Inc., Naperville, Ill.) which contains a mixture of fatty acids, phospholipids, lipoproteins and cholesterol.

Serotonin (5-hydroxytryptamine) is found predominantly in enterochromaffin cells throughout the gastrointestinal tract, in platelets and in parts of the brain. It is known to be a potent neurotransmitter. It stimulates and inhibits nerves and smooth muscles in the cardiovascular, respiratory and gastrointestinal systems. Serotonergic agonists, which mimic the effect of serotonin when interacting with one of its receptor, have been identified and include for example, ipsapirone, gepirone, buspirone, 1-[2-(4-aminophenyl)-ethyl]4-(3-bbyfluromethyl phenyl) piperazine (PADD) and N,N-dipropyl-5-carboxamidotryptamine (DP-5CT). Further, see Hamon et al, in the Neuropharmacology of Seratonin, Whitabker-Azmitia and Perouthka (eds), Ann. N.Y. Acad. Sci., 600:114, 1990. It has been discovered in accordance with the invention that serotonin and its agonists exert a mitogenic activity on hMSC when included in the Chemically Defined Medium.

Sodium pyruvate can also be added to the formulation to supplement its availability for the Kreb's cycle. Biotin can also be added to the formulation to supplement its availability as an coenzyme important in carboxyl group transfer reactions. Vitamin B12 (cyanocobalamin) or its coenzyme precursor (cobalamin) can also be added to the formulation to supplement its availability as a coenzyme for group transfer and methylation reactions. Trace element mix can also be added to the formulation to provide a supplemental source of metals necessary for electron transport and many metalloenzymes and proteins. Nucleoside mix can also be added to the formulation as a supplemental source of purine and pyrimidine bases necessary for DNA and RNA synthesis.

EXAMPLE 1

Culture Expansion of Human MSCs in a Serum-Free Medium

Isolation and Preparation of Human MSCs

Human bone marrow cells were from marrow aspirated from the iliac crest of normal donors. The donors included both female and male ranging in age from 19 to 52 years.

Human mesenchymal stem cells (MSC) were purified and cultured using a modification of a previously reported method (Haynesworth et al., 1992a). Iliac crest marrow (20 to 40 ml) was vortexed to disperse the cells. The marrow was equally divided between three 50 ml centrifuge tubes each containing 20 ml of Dulbecco's Modified Eagles Medium (DMEM) supplemented with fetal bovine serum (10% v/v) from selected lots (BioCell) (Complete Medium). The cells were pelleted by a 5 minute spin at 1200 rpm in a Beckman GS-34 table top centrifuge fitted with a GH 3.8 horizontal rotor (Beckman). The cell pellets (5.0 ml) were, layered over preformed gradients of 70% Percoll. The cells were fractionated by centrifuging the gradients at 460×g for 15 minutes. The MSCs were isolated from the top 25% of the gradient, transferred to a 50 ml centrifuge tube and rinsed with 30 ml of complete medium. The cells were counted using a hemacytometer, after lysing the red blood cells. The cells were plated onto 100 mm tissue culture plates at $1\times10^7$ cells per dish. The cultures were maintained at 37° C. in a humidified atmosphere of 95% air and 5% $CO_2$ and the culture medium was changed every 3 to 4 days.

Culturing and Passaging of Human MSC

When the colonies on the plates became large and near confluent the cells were lifted off the plates by incubating the cells with 0.25% trypsin containing 1 mM EDTA (GIBCO) for 5 minutes at 37° C. The trypsin reaction was quenched by adding bovine calf serum (Hyclone) at half the volume of the cell sample. The cells were replated at a ratio of 1:3. The first passage cultures were subcultured again when the cultures reached 80% to 90% confluence.

The screening of components to be added to the serum free Chemically Defined Medium (CDM) was done using second or third passage cells seeded onto 35 mm dishes at a density of $2.5\times10^4$ cells in Complete Medium. A seeding density of $3\times10^4$ was used for the in vitro osteogenesis assay. The cells were allowed to attach for 24 hours. After the cells had attached, the medium was removed, the cell layer was rinsed with serum free DMEM and the serum free formulation containing the test components was added. Each component was tested in triplicate and repeated a second time with a different donor sample. The medium was changed as usual and the cells examined daily under an Olympus microscope.

Serum-Free Human Chemically Defined Medium (hCDM)

The minimum essential medium for the serum free formulation of this example was Iscove's modified Dulbecco's Medium (IMDM) (Gibco). IMDM was supplemented with human serum albumin (Miles) 5 mg/ml, human Ex-Cyte lipoprotein (Miles) 100 μg/ml, saturated human transferrin (Boehringer Mannheim) 2 μg/ml, human recombinant insulin (Boehringer Mannheim) 10 μg/ml, 100×MEM vitamins (Sigma) 1.0% MEM essential amino acids (Gibco) 0.89% MEM nonessential amino acids (Gibco) 0.4% sodium pyruvate (Gibco) 1 mM, GlutaMAX-I supplement (Gibco) 1 mM, folic acid (Gibco) 10 μg/ml, Ascorbic acid 2-phosphate (Whako BioProducts) 10 μM, Biotin (Gibco) 1.0 μg/ml, vitamin B12 mix (Gibco) 1.36 μg/ml, trace element mix (Gibco) diluted 500 fold, $FeSO_4$ (Sigma) $4\times10^{-8}$M, nucleoside mix (Sigma ribonucleosides, 2'-deoxyribonucleosides, uridine, and thymidine) 10 μg/ml, antibiotic/antimycotic (Gibco) 1.0%, and either human recombinant PDGF ββ homodimer (Boehringer Mannheim) 10–20 ng/ml or 5-hydroxytryptamine (Sigma) $10^{-5}$ to $10^{-6}$M.

Cell Proliferation Assay

The rate of cell proliferation was measured by a colorimetric dye binding assay using crystal violet dye. The method used was a modification of the methods described by Westergen-Thorsson et al. (1991) and Lennon et al. (1995). Since crystal violet is specific for the nucleus of the cell the intensity of staining is proportional to cell number and can be quantified by measuring the absorbance of the extracted dye at 595 nm. For each batch of crystal violet a standard curve was generated using a fixed number of MSCs ($5\times10^3$ to $1\times10^5$ cells/35 mm dish). The slope of the line (correlation coefficient=0.99) was used to calculate the cell number in each the test well. For the proliferation assay, human MSCs were plated into 35 mm plates at 2.5 to $3\times10^4$ cells per plate. The plates were removed on day 7 from 37° $CO_2$ incubator. The cell layer was rinsed 2 times with 1.0 ml of Tyrode's balanced salt solution, and then was fixed for 15 minutes with 1.0 ml of 196 (v/v) glutaraldehyde in Tyrode's. The cell layer was rinsed 2 times with 1.0 ml $H_2O$ and allowed to air dry. The cells were stained with 0.1% (v/v) Crystal Violet in $H_2O$ for 30 minutes at ambient temperature. The plates were rinsed 3 times with $H_2O$ and the bound dye was extracted by adding 2.0 ml of 1.096 (v/v) Triton X100 in $H_2O$ to each plate and gently agitating on a rotating shaker for 4 hours at room temperature.

The extracted dye (200 μl) was transferred to a well of a 96 well plate and the absorbance measured at 595 nm on an ELISA plate reader (BioRad) using 1.0% Triton X100 as a blank.

Alkaline Phosphatase Histochemistry

The level of alkaline phosphatase activity of human MSCs was measured using an alkaline phosphatase kit (Sigma). The plates were removed from a 37° $CO_2$ incubator at set time points, rinsed 2 times with 1.0 ml of PBS and fixed for 1 minute with a citrate/acetone solution. The cells were rinsed 2 times with $H_2O$ (1.0 ml) before adding 2.0 ml of Fast Violet Solution (0.5 ml of Napthol AS-MX Phosphate alkaline solution in 12 ml of Fast violet solution) to each plate. The plates incubated in the dark at room temperature for 1 hour, the cells were then rinsed 2 times with $H_2O$ and air dried before microscopic examination.

Quantification of Alkaline Phosphatase Activity

The cell layer were washed 2 times with Tyrode's (2.0 ml). Substrate, p-nitrophenol phosphate (Sigma 104 tablet 5.0 mg), dissolved in substrate buffer (50 mM glycine pH 11, 1.0 mM MgCl) (1.0 ml), was added to each plate. The plates were incubated at 37° C. for 5 to 20 minutes. The amount of released p-nitrophenol (PNP) was measured at 405 nm in an ELISA plate reader. Enzyme activity was expressed both as PNP released $min^{-1}$ and PNP $min^{-1}.10^6$ $cell^{-1}$.

Von Kossa Staining of Mineralized Nodules

Plates were rinsed 2 times with Ca and Mg free Phosphate buffered saline (2.0 ml). The cells were fixed for 1 hour with 10% buffered formalin and then the plates were rinsed 2 times with H$_2$O (2.0 ml). A 2% (w/v) AgNO$_3$ in H$_2$O (1.0 ml) and incubate at in the dark for 10 minutes. The plates were rinsed with H$_2$O (3×2.0 ml). With the last rinse left on the plates, they were exposed to a bright light for 15 minutes. The plates were rinsed again with H$_2$O and air dried.

Alkaline Phosphatase Activity and Mineralized Nodule Formation by Cultures Grown in Serum Free Medium Supplemented With Dexamethasone Alkaline phosphatase activity and mineralized nodule formation was determined using medium supplemented with dexamethasone ($10^{-7}$M), ascorbic acid-2-phosphate (0.05 mM), and β-glycerophosphate (10 mM) osteogenic supplements (OS). Confluent first or second passage cells were subcultured into 35 mm dishes at a density of 3.0×10$^4$ cells per dish. Cells were allowed to attach as usual. The medium was removed and replaced with either serum free medium or serum free medium containing OS. Complete Medium was used as a positive control. On days 4, 8, 12, and 16 the cultures were removed from a 37° CO$_2$ incubator and cell proliferation, alkaline phosphatase activity (histochemical and biochemical) and mineralized nodule formation were measured.

Preparation of Human MSC for Ceramic Cube Assay

Cultured MSCs were trypsinized from the plate as described above. The cells were rinsed with serum free medium (2×10 ml) and counted. The cell density was adjusted to 5×10$^6$ cell per ml with serum free medium. Porous 3 mm$^3$ ceramic cubes composed of a mixture of 60% tricalcium phosphate and 40% hydroxyapatite (Zimmer Corporation, Warsaw, Ind.), and prepared as described by Dennis et al. (1992) and Lennon et al. (1995), were added to the cell suspension. A slight negative atmospheric pressure was generated by evacuating 10 ml of air to ensure that the cells would infiltrate into the pores of the cubes. The cubes with cells were incubated at 37° C. for 1 to 2 hours prior to implanting into severe combined immunodeficiency (SCID) mice.

Immunocytochemical Staining

Human MSCs (1st to 3rd passage) in Complete Medium were seeded into 35 mm dishes at 30,000 cells per dish and the cells were allowed to attach for 16 hours before switching to the serum free medium. The cells were grown in the test medium for 3 to 4 days and control plates were left in Complete Medium. The cells were rinsed three times with PBS. the cultures were incubated for 1 hour with 100 μl of either SH2 or SH4 hybridoma culture supernatant (Haynesworth et al., 1992b). Chick specific SB1 Bruder et al. hybridoma supernatant was used as a negative control. Plates were rinsed with a 0.1% BSA in PBS solution (3×2.0 ml) and incubated for 45 minutes with an FTTC-conjugated goat antimouse IgG diluted in 0.1% BSA-PBS. The dishes were again rinsed with 0.1% BSA-PBS (3×2.0 ml). The cell layer was covered with a coverslip after a drop of PPD immunofluorescence mounting medium was added. Immunofluorescence was observed on an Olympus BX50 epifluorescence microscope.

RESULTS

Human MSC Proliferation in Serum Free Medium

Figure 1A:
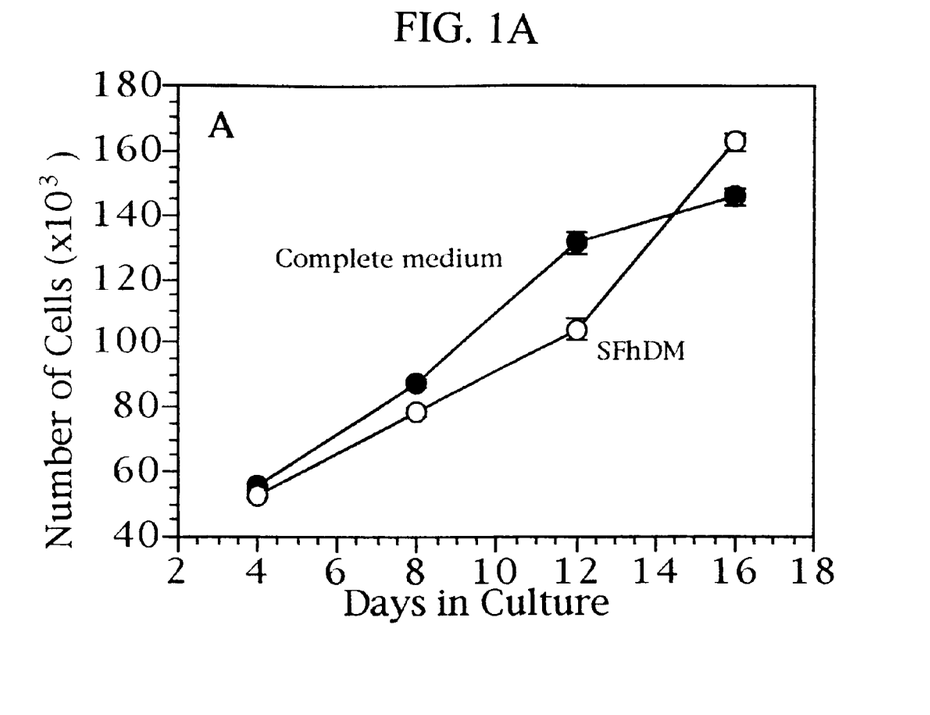
FIGS. 1A and 1B each graphically illustrate comparisons of human MSC proliferation when cultured in the Chemically Defined Medium (containing PDGF-$\beta\beta$) of the invention or in Complete Medium (containing serum) which were made by a crystal violet dye binding assay.
Figure 1B:
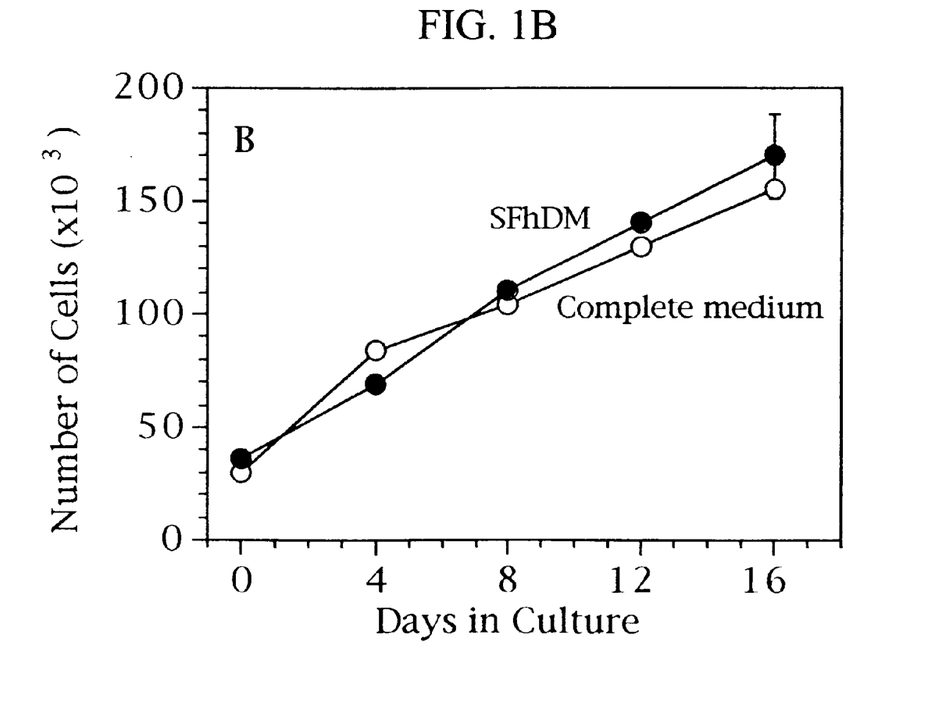

The growth kinetics of human MSCs in serum free medium was measured using the crystal violet dye binding assay with MSCs grown in Complete Medium as a positive control,. When human MSCs were cultured in CDM containing 10 ng/ml of PDGF-ββ, they exhibited growth kinetics similar to those cells grown in Complete Medium (FIGS. 1A and 1B). The proliferation of cells maintained in CDM was generally between 80 to 90% of that observed in the cultures maintained in Complete Medium. The cell proliferation, however, declined slightly at days 10 to 12. Since these cultures were generally between 80 to 90% confluent by day 8 the decrease in cell proliferation observed beyond day 8 was not considered problematic. Passage of cells grown in CDM generally returned the proliferative capacity of these cells in CDM.

Figure 2A:
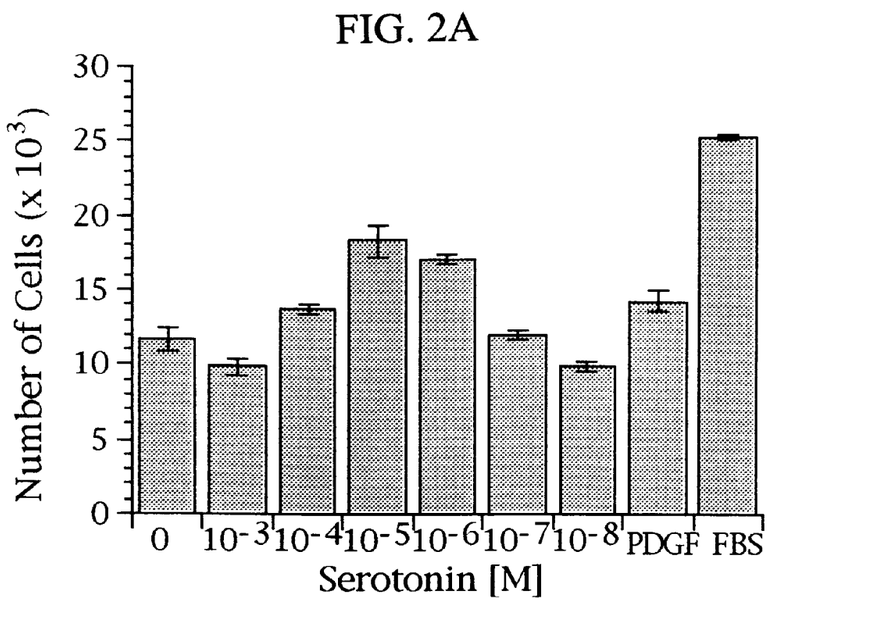
FIGS. 2A and 2B graphically illustrate the MSC proliferative response observed when human MSCs were grown for 6 days in the Chemically Defined Medium of the invention with the presence of a range of serotonin concentrations and in the presence or absence of PDGF, respectively.
Figure 2B:
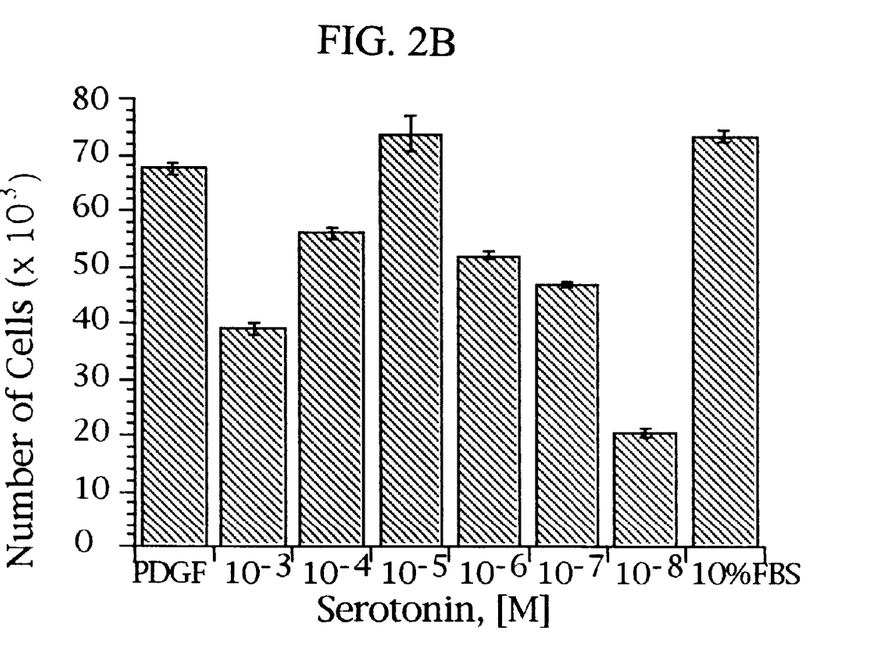

Lauder, TINS, 16:233–239, 1993, has suggested that 5-hydroxytrypamine (5HT) may be involved in regulation of morphogenic activities such as cell proliferation and differentiation. To determine if 5HT was able to simulate the proliferation of human MSCs, a dose response evaluation was made using the crystal violet cell proliferation assay. Human MSC were grown in either CDM, with or without PDGF in the presence of increasing concentrations of 5HT for six days. (FIGS. 2A and 2B respectively). As illustrated in the figures there is a dose response effect of 5HT on cell number. The optimum concentration for MSC proliferation appears to be between $10^{-5}$M to $10^{-6}$M of 5HT.

Cell Morphology

In addition to the measuring proliferation of human MSC grown in CDM it was also important that the cells maintain the correct morphology, one that is similar to that seen in cultures maintained in Complete Medium. Human MSC from first, second and third passages maintained in Complete Medium have the same morphology, most cells having a fibroblastic morphology, with a few polygonal, or rounded cells.

Figure 3A:
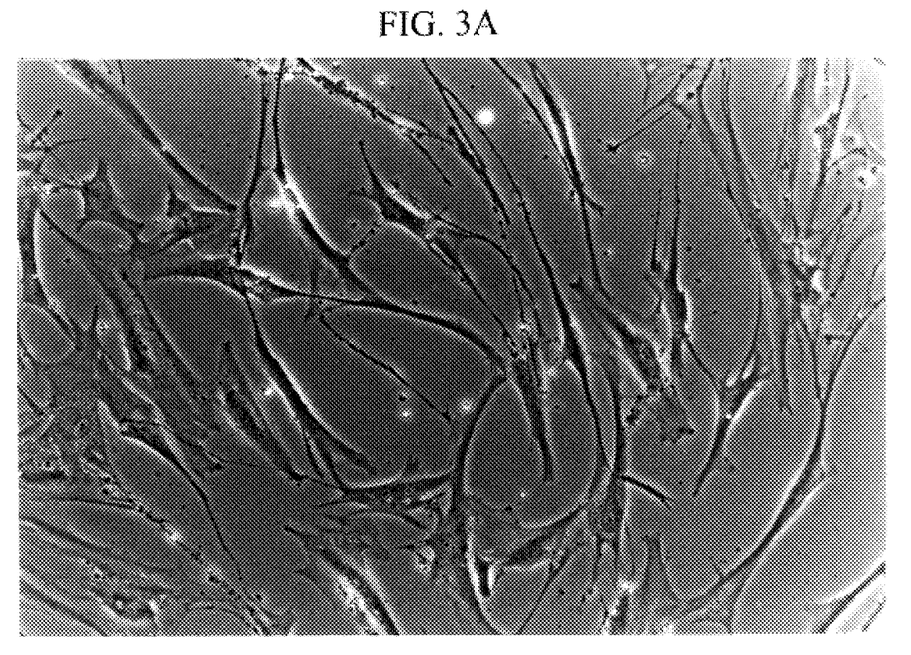
FIGS. 3A and 3B are photomicrographs of human MSCs cultured in Complete Medium and the Chemically Defined Medium (CDM) of the invention, respectively.
Figure 3B:
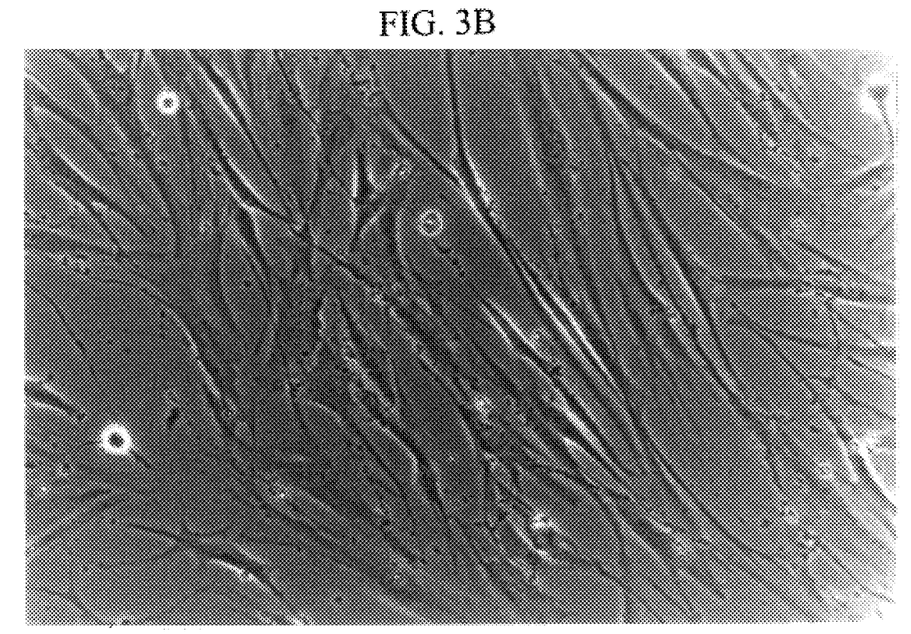

Human MSCs maintained in CDM had a morphology that was similar to that of cells grown in Complete Medium (FIG. 3). The majority of the cells had the same spindle shaped fibroblastic morphology as the cells grown in Complete Medium. There were also some larger rounded cells in the CDM cultures, but these cells were a small minority.

In Vitro Osteogenesis of Human MSC in SFHDM

Figure 4A:
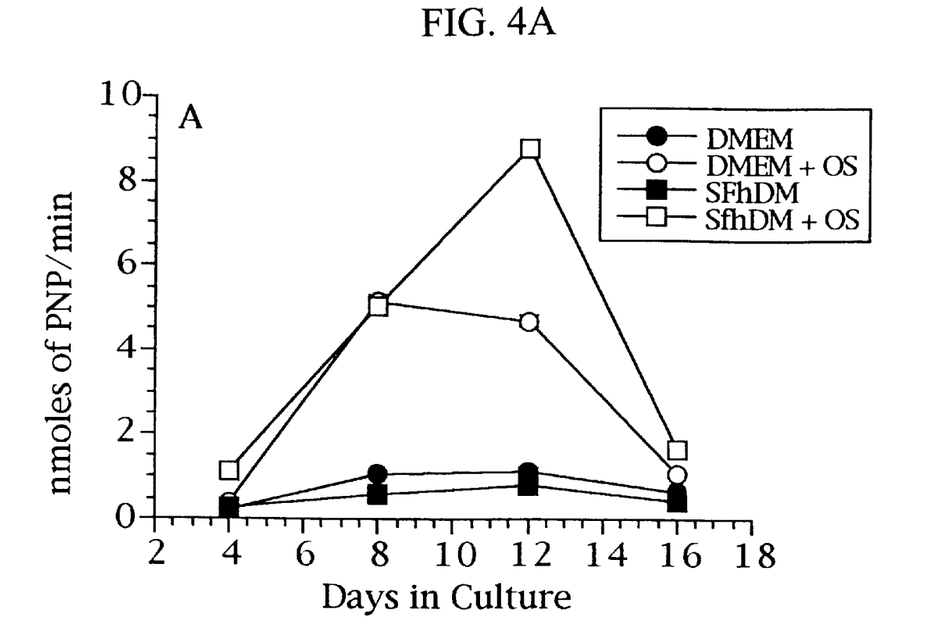
FIG. 4A shows that cells grown in Chemically Defined Medium with OS exhibited an increase in alkaline phosphatase activity that was higher than that of cells in CDM without OS and that was comparable to that of cells grown in Complete Medium with OS.
Figure 4B:
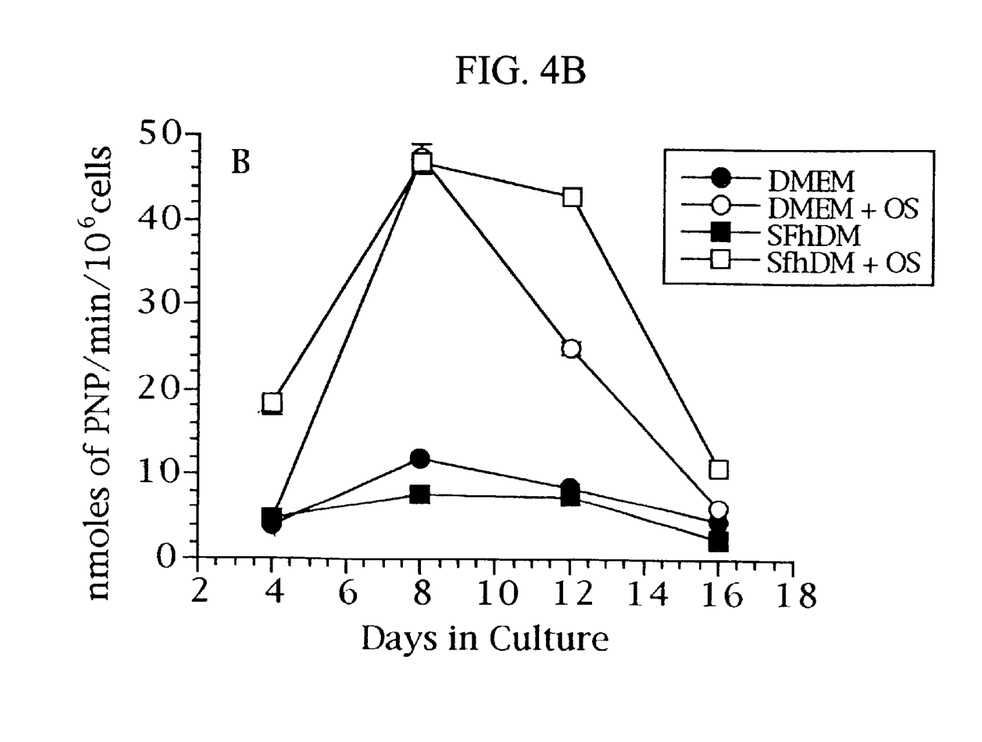
FIG. 4B shows that this observed increase was still apparent when the alkaline phosphatase was normalized with respect to cell number.

Dexamethasone, β-glycerophosphate and ascorbate 2-phosphate was added to the CDM (OS) to measure the in vitro osteogenic potential of human MSCs grown in CDM. Human MSC were grown in CDM+PDGFββ with and without OS for 16 days. The level of osteogenic differentiation alkaline phosphatase activity (histochemically and biochemically) and the degree of mineralized nodule formation were measured at days 4, 8, 12, and 16. The positive control for these assays was human MSC grown in Complete Medium with and without OS. The cells grown in CDM+OS exhibited an increase in alkaline phosphatase activity that was higher than that of cells in CDM and the same as that of cells grown in complete medium+OS (FIG. 4A). This observed increase was true even when alkaline phosphase activity was normalized to cell number (FIG. 4B). The histochemical stamina mirrored that of the biochemical activity. There was an increase in the number of alkaline phosphatase positive cells in the culture maintained in CDM+OS. This staining pattern was similar to that of cells grown in Complete Medium+OS. On day 16 the alkaline phosphatase positive cells in both the cultures maintained in CDM+OS and Complete Medium+OS had a rounded and polygonal morphology. The cells maintained in either CDM or Complete Medium on day 16 did not lose their fibroblastic morphology. This was true for both alkaline phosphatase positive and negative cells.

The appearance of Von Kossa positive staining nodules were apparent by day 16 in both the CDM+OS and Complete Medium+OS cultures. These cells had Von Kossa positive nodules beginning on day 12 and increasing in number through day 16. Cells maintained in either CDM or Complete Medium never developed Von Kossa positive nodules.

In Vivo Bone Formation in Ceramic Cubes

The osteochondrogenic potential of human MSC has been demonstrated by their ability to form bone when loaded into ceramic cubes and implanted subcutaneously into Nude mice (Haynesworth et al., 1992a). To determine the osteochondrogenic potential of human MS's grown in CDM these cells were grown in CDM, loaded into ceramic cubes and implanted into SCID mice. SCID mice were used because there is no immunological response to human cells. Human MSCs, 1st or 2nd passage, were subcultured in completed medium onto 100 mm tissue culture plates at a density of $3\times10^5$ cells per dish. After the cells attached (16 hours), the cultures were rinsed 2 times with sterile Tyrode's before switching to CDM+PDGF. The MSCs were grown in this medium until the cultures became near confluent. The MSCs were then harvested, loaded into ceramic cubes and implanted subcutaneously into SCID mice. The cubes were harvested at 3 weeks and 6 weeks.

Ceramic cubes loaded with control MSCs or MSCs grown in CDM were negative for bone 3 weeks post implantation. Six weeks post-implantation cubes containing either cells grown in CDM or Complete Medium were positive for bone. After 6 weeks of incubation in SCID mice, bone was observed in 90 to 100% of the ceramic cubes containing control MSC as compared to 85% to 90% of the cubes which contained MSCs grown in CDM+PDGF contained bone.

Immunohistochemical Staining of MSC

To further characterize cells grown in CDM these cells were probed for their expression of the SH antigens characteristic of human MSCs (Haynesworth et al., 1992b). The immunoreactivity of antibodies SH4 and SH2 to human MSCs from 2nd passage was evident in both cells grown in CDM and Complete Medium. There was no observed difference in reactivity of the SH antibodies to human MSC when maintained in either Complete Medium or CDM. The antibodies and the reactivity was much greater with SH4 than SH2. This was also true for cells maintained in complete medium.

What is claimed is:

1. A method for culturally expanding human mesenchymal stem cells comprising culturing an isolated homogenous population of viable human mesenchymal stem cells for a suitable time in a serum free medium which comprises (1) a minimum essential medium; (2) serum albumin; (3) an iron source; (4) insulin or an insulin-like growth factor; (5) glutamine; and (6) a mitogen selected from the group consisting of platelet derived growth factor and serotonin, which are present in amounts effective to culturally expand the human mesenchymal stem cells.

2. The method of claim 1 wherein the iron source is transferrin.

3. The method of claim 1 wherein the insulin-like growth factor is IGF-1 or IGF-2.

4. The method of claim 1 wherein the serum free medium further includes a lipid.

5. The method of claim 1 wherein the serum free medium further includes an antioxidant.

6. The method of claim 5 wherein the antioxidant is ascorbic acid or an analog or derivative thereof.

7. A composition which comprises an isolated homogenous population of viable human mesenchymal stem cells in a serum free medium comprising (1) a minimum essential medium; (2) serum albumin; (3) an iron source; (4) insulin or an insulin-like growth factor; (5) glutamine; and (6) a mitogen selected from the group consisting of platelet derived growth factor and serotonin which are present in amounts effective to culturally expand the human mesenchymal stem cells in the absence of serum.

8. The composition of claim 7 wherein the iron source is transferrin.

9. The composition of claim 7 wherein the insulin-like growth factor is IGF-1 or IGF-2.

10. The composition of claim 7 wherein the composition further includes a lipid.

11. The composition of claim 7 which further includes an antioxidant.

12. The composition of claim 11 wherein the antioxidant is ascorbic acid or an analog or derivative thereof.

* * * * *